(12) United States Patent
Fudge et al.

(10) Patent No.: US 7,137,390 B2
(45) Date of Patent: Nov. 21, 2006

(54) LIQUID ABSORBING FILTER ASSEMBLY AND SYSTEM USING SAME

(75) Inventors: Brian M Fudge, Middletown, CT (US); John A Triunfo, Jr., Fairfield, CT (US); David R Rich, Glastonbury, CT (US)

(73) Assignee: RIC Investments, LLC., Wilmington, DE (US)

( * ) Notice: Subject to any disclaimer, the term of this patent is extended or adjusted under 35 U.S.C. 154(b) by 0 days.

(21) Appl. No.: 11/039,749

(22) Filed: Jan. 19, 2005

(65) Prior Publication Data

US 2005/0161042 A1    Jul. 28, 2005

Related U.S. Application Data

(60) Provisional application No. 60/538,766, filed on Jan. 23, 2004.

(51) Int. Cl.
*A62B 19/00*    (2006.01)

(52) U.S. Cl. .................................................. 128/205.12

(58) Field of Classification Search ........... 128/205.12, 128/205.27, 205.28, 205.29, 205.23, 201.13, 128/204.13, 204.17
See application file for complete search history.

(56) References Cited

U.S. PATENT DOCUMENTS

| | | | |
|---|---|---|---|
| 3,631,654 A * | 1/1972 | Riely et al. ..................... 96/6 |
| 4,031,891 A * | 6/1977 | Jess ............................ 604/126 |
| 4,262,668 A * | 4/1981 | Schmidt ...................... 604/126 |
| 4,424,817 A * | 1/1984 | Williams ..................... 600/579 |
| 4,571,244 A * | 2/1986 | Knighton ..................... 604/118 |
| 4,938,389 A * | 7/1990 | Rossi et al. ............. 222/189.08 |
| 5,131,387 A | 7/1992 | French et al. |
| 5,616,158 A | 4/1997 | Biendarra et al. |
| 6,375,854 B1 * | 4/2002 | Beplate ...................... 210/767 |
| 6,550,347 B1 * | 4/2003 | Bradley .................... 73/863.21 |
| 6,783,573 B1 * | 8/2004 | Richardson ...................... 96/6 |

* cited by examiner

*Primary Examiner*—Henry Bennett
*Assistant Examiner*—Dinnatia Doster-Greene
(74) *Attorney, Agent, or Firm*—Michael W. Haas

(57) ABSTRACT

A filter assembly for use in sidestream gas sampling assembly. The filter assembly of the present invention includes a hydrophilic liner lining the inner perimeter of a housing for wicking moisture from the gases to be monitored prior to the gases reaching a sensing mechanism. The filter further includes a hydrophobic member positioned downstream of the hydrophilic liner. The hydrophobic disk acts as a second line of defense against moisture reaching the sensing mechanism. In one embodiment, the filter further include an absorbent layer positioned between the cylindrical housing and the hydrophilic layer to aid in wicking moisture from the gas stream. In a further embodiment, the hydrophobic disk is eliminated and the hydrophilic member is situated such that gas entering the filter assembly must pass through at least a portion the hydrophilic member.

20 Claims, 4 Drawing Sheets

LIQUID ABSORBING FILTER ASSEMBLY AND SYSTEM USING SAME

CROSS-REFERENCE TO RELATED APPLICATIONS

This application claims priority under 35 U.S.C. § 119(e) from provisional U.S. patent application No. 60/538,766 filed Jan. 23, 2004 the contents of which are incorporated herein by reference.

BACKGROUND OF THE INVENTION

1. Field of the Invention

The present invention relates generally to a sidestream gas monitoring system for monitoring a patient's medical condition, and, in particular, to a filter assembly for use in a sidestream monitoring system that separates undesired liquid components from respiratory gases to be monitored.

2. Description of the Related Art

During medical treatment, it is often desirable to monitor and analyze a patient's exhalations to determine the gaseous composition of the exhalate. For instance, monitoring the carbon dioxide ($CO_2$) content of a patient's exhalations is often desirable. Typically, the carbon dioxide (or other gaseous) content of a patient's exhalation is monitored by transferring a portion, or sample, of the patient's expired gases to a suitable sensing mechanism and monitoring system.

Monitoring of exhaled gases may be accomplished utilizing either mainstream or sidestream monitoring systems. In a mainstream monitoring system, the gaseous content of a patient's exhalations is measured in-situ in the patient circuit or conduit coupled to the patient's airway. In a sidestream monitoring system, on the other hand, the gas sample is transported from the patient circuit through a gas sampling line to a sensing mechanism located some distance from the main patient circuit for monitoring. As a patient's expired gases are typically fully saturated with water vapor at about 35° C., a natural consequence of the gas transport is condensation of the moisture present in the warm, moist, expired gases.

Accurate analysis of the gaseous composition of a patient's exhalation is dependent upon a number of factors including collection of a gaseous sample that is substantially free of liquid condensate, which might distort the results of the analysis. As an expired gas sample cools during transport through the gas sampling line to the sensing mechanism in a sidestream monitoring system, the water vapor contained in the sample may condense into liquid, i.e., condensate. The liquid, i.e., condensate, if permitted to reach the sensing mechanism, can have a detrimental effect on the functioning thereof and may lead to inaccurate monitoring results. Condensed liquid in the gas sampling line may also contaminate subsequent expired gas samples by being re-entrained into such subsequent samples.

In addition to the condensate, it is not uncommon to have other undesirable liquids, such as blood, mucus, medications, and the like, contained in the expired gas sample. Each of these liquids, if present in the gas sample to be monitored, may render analytical results that do not accurately reflect the patient's medical status.

There are numerous techniques for separating undesired liquids from the patient's expired gas stream to protect the gas sensing mechanism. For instance, it is known to place a moisture trap between the patient and the sensing mechanism to separate moisture from the exhalation gas before it enters the sensing mechanism. The challenge, however, is to achieve the separation without affecting the characteristics of the parameters being measured, e.g., the waveform of the gas to be monitored.

By way of example, carbon dioxide ($CO_2$) is effectively present only in the patient's expired gases. Therefore, the $CO_2$ in an exhaled gas sample, transported through a gas sampling line to the sensing mechanism, fluctuates according to the $CO_2$ present at the point at which the sample is taken. Disturbances in this fluctuation, i.e., in the $CO_2$ waveform, are undesirable because any such disturbance can affect the accuracy of the $CO_2$ measurement and the graphical display of the waveform. For this reason, removal of liquids from the exhaled gas sample is desirably accomplished in such a way that it does not substantially disturb the $CO_2$ waveform. Unfortunately, conventional moisture traps often disturb the waveform to a substantial degree.

Various other techniques have been employed to filter the expired gas stream of the undesired condensate while attempting to permit the waveform to be transported undisturbed. Such techniques include absorbents for wicking condensate out of the gas, centrifugal filters, desiccants, hydrophobic membranes for filtering gases and hydrophilic membranes for filtering liquids. While each of these techniques has its advantages, each has its drawbacks as well. Each of the techniques listed above can remove a portion of the liquid condensate, but none is foolproof, except, perhaps for those using a hydrophobic filter. A consequence, a portion of the liquid condensate may still reach the sensing mechanism in many conventional filters. On the other hand, conventional filters that use a hydrophobic filter, can disturb the waveform beyond acceptable levels. Accordingly, a suitable filter that does not substantially disturb the waveform of expired gases and while substantially separating moisture from the gas sample and while minimizing deadspace would be advantageous.

SUMMARY OF THE INVENTION

Accordingly, it is an object of the present invention to provide a filter assembly that overcomes the shortcomings of conventional filter assemblies. This object is achieved according to one embodiment of the present invention by providing a low deadspace filter assembly for use in sidestream gas sampling system that includes a housing lined along the inner wall thereof with a hydrophilic liner for wicking moisture out of the expired gases. In one embodiment, the hydrophilic liner lines the inner perimeter of the cylindrical housing substantially along its entire axial length, excepting a portion at the downstream-most end thereof where a hydrophobic member and an exit conduit are located. The hydrophobic member extends across the inner diameter of the channel through cylindrical housing near the downstream end thereof. The housing is adapted to be coupled in a gas-tight and fluid-tight arrangement with a gas sampling line through which expired gases may be received.

In use, expired gases enter the filter assembly through the gas sampling line and proceed through the housing. The hydrophilic liner wicks moisture out of the expired gases and absorbs such liquids preventing them from reaching the gas monitoring system. The gases, and any moisture not absorbed by the hydrophilic liner, proceed through the housing to the downstream end where they encounter the hydrophobic member. The hydrophobic member permits the passage of gases therethrough but substantially prevents the passage of liquids. Thus, even moisture that did not get absorbed by the hydrophilic liner is prevented from reaching the sensing mechanism as it is not permitted to pass through the hydrophobic member. In this manner, only gases substantially free of liquid condensate are permitted to reach the gas monitoring system. Further, because only the inner perimeter of the cylindrical housing is lined with filter material until the gases reach the hydrophobic member, the waveform of the exhaled gas sample is permitted to proceed substantially undisturbed from the point at which the sample is collected to the point at which the sensing mechanism readings are taken. Disturbance to the waveform which may be caused by the hydrophobic disk is minimal.

In an alternative embodiment, the filter assembly of the present invention further includes an absorbent layer positioned between the inner perimeter of the cylindrical housing and the hydrophilic liner. The absorbent material has a higher absorbance than the hydrophilic layer and further aids in wicking moisture from the expired gases and locking it away from the gases to be monitored.

In a further embodiment, the hydrophobic disk is eliminated. The hydrophilic member is situated in the housing such that gas entering the filter assembly must pass through at least a portion the hydrophilic member.

The present invention also pertains to sidestream gas monitoring system that includes either of the above-described filter assembly embodiments.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE PRESENTLY PREFERRED EMBODIMENTS OF THE INVENTION

Figure 1:
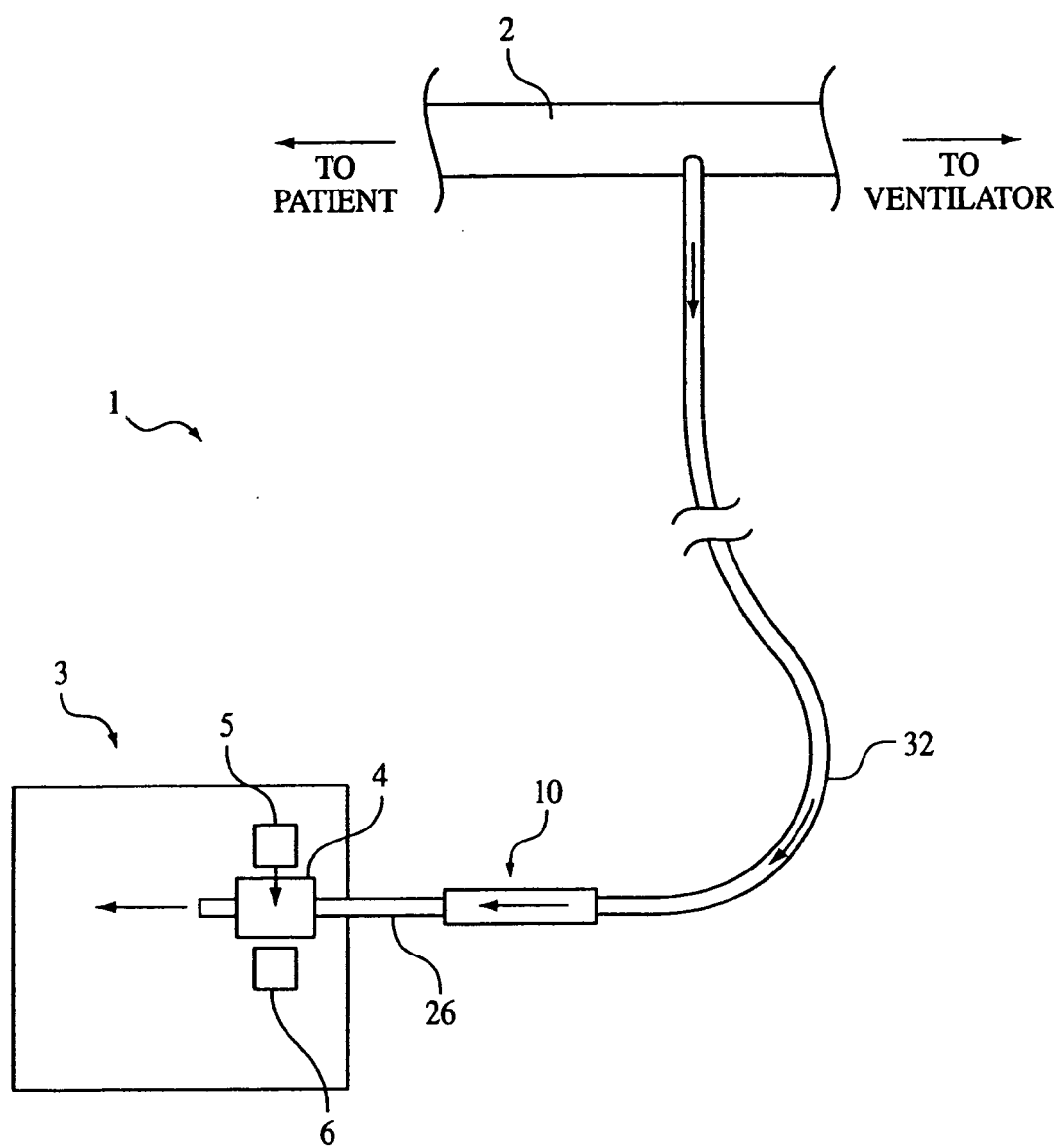
FIG. 1 is a schematic view of a sidestream gas monitoring system including a filter assembly according to the principles of the present invention.

Referring to the drawings in general and initially to FIG. 1, in particular, an exemplary embodiment side stream gas monitoring system 1 including a filter assembly 10 according to the present invention is illustrated. Gas monitoring system includes a sampling line 32 that is coupled to a patient circuit 2, which is, in turn, in connected to an airway of patient (not shown) so that a portion of the gas in the patient circuit is diverted into sampling line 32. Filter assembly 10 is coupled to an end of the sample line distal from the patient circuit and proximate to a gas monitoring system, generally indicated at 3.

The present invention contemplates that gas monitoring system 3 is any conventional sidestream gas monitoring system, which typically includes a sample cell 4 and a system for measuring the constituents of the gas within the sample cell. Such a system may include, for example, a radiation emitter 5 and receiver 6, which detects the gas constituents within the sample cell using well know radiation absorption techniques. The present invention also contemplates using any suitable technique to attach the gas monitoring system to the airway of the patient. For example, the present contemplates using an airway adapter connected to the patient circuit with a sampling line. This configuration is shown in FIG. 1. Alternatively, a nasal cannula can be used to connect the sampling line to the airway of the patient.

Figure 2:
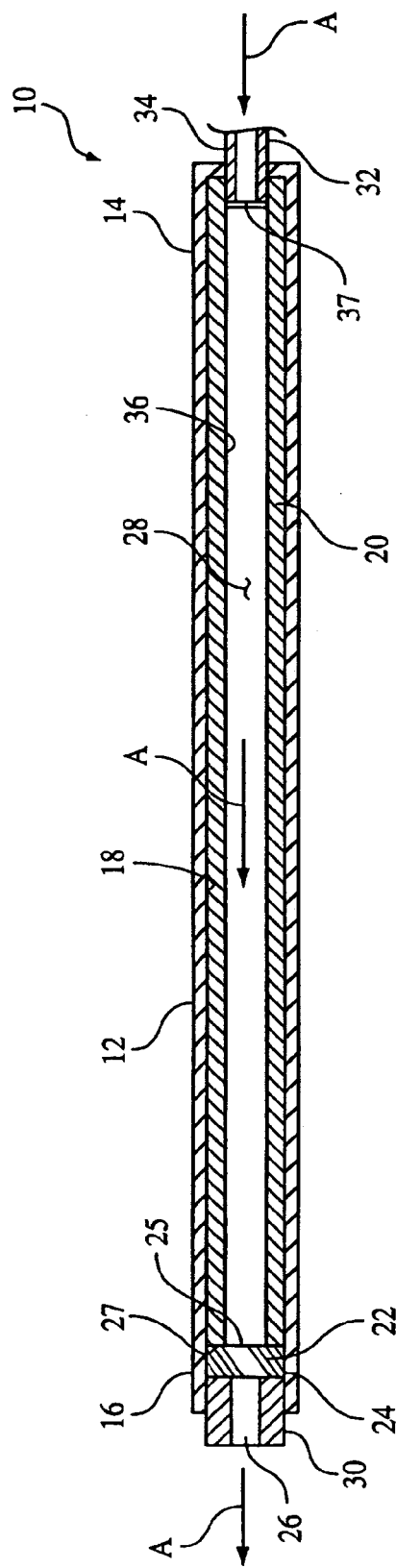
FIG. 2 is a cross-sectional view of a first embodiment of the filter assembly.

Referring now to FIG. 2, which is 2 is a cross-sectional view of a first embodiment of filter assembly 10, the filter assembly includes a housing 12 typically formed of a suitable polymer and having a cylindrical shape. Of course, other materials and shapes are contemplated by the present invention. Housing 12 includes axially opposed first and second ends 14, 16 and has an inner diameter defined by an inner wall 18 thereof. During normal use, gas is carried from the patient circuit into first end 14 via a sampling line 32 connected to the first end. The gas passes through a channel 28 defined in housing 12 and exits second end 16, where it is provided to gas monitoring system 3 of FIG. 1. The flow of gas through filter assembly 10 is indicated by arrows A.

Lining inner wall 18 of housing 12 is a hydrophilic liner 20 for wicking moisture from expired gases and locking it away from the gas stream, as more fully described below. The present invention contemplates that hydrophilic liner 20 be formed of a material suitable for accomplishing the wicking function, such as a porous plastic, having a pore size ranging from approximately 5 microns to approximately 50 microns. The present invention contemplates that hydrophilic liner 20 is coupled with inner wall 18 of housing 12 by any technique known to those of ordinary skill in the art including, but not limited to, adhesives. Hydrophilic liner 20 not only absorbs moisture, but also acts as a smooth lining for housing 12, and thereby minimizes turbulence in the gas stream which may be caused by rough walls.

A hydrophobic member 22 is provided at the downstream end of housing 12, i.e., proximate to second end 16. In the illustrated embodiment, hydrophobic member 22 is a disc that spans the interior of the housing, i.e., extends across the inner diameter of channel 28. More specifically, hydrophobic member 22 has an outer diameter, defined by an outer surface 24 thereof that approximates the inner diameter of housing 12 such that the outer surface of the hydrophobic member is coupled with inner wall 18 of housing 12 in a gas-tight and fluid-tight arrangement. Such fluid-tight and gas-tight coupling mechanisms are known to those of ordinary skill in the art and, accordingly, will not be discussed further herein. In this manner, only gases passing through hydrophobic member 22 are permitted to reach the gas monitoring system 3, as more fully described below. An upstream surface 25 of the hydrophobic disk is in contact with a downstream edge 27 of the hydrophilic liner 20.

In the illustrated exemplary embodiment, hydrophilic liner 20 lines inner wall 18 of cylindrical housing 12 from first end 14 to a point near second end 16 where hydrophobic member 22 is located. It is to be understood, however, that hydrophilic liner 20 need not extend along the entire length of the housing, need not cover the entire surface of inner wall 18, and need not be formed from a single, unitary material. Rather, hydrophilic liner 20 can be formed from multiple pieces of material, and each portion or piece of the liner need not be formed from the same material. For example, the liner can be formed such that the absorbency of the material changes along the length of the housing.

Positioned downstream of hydrophobic member 22 and in contact therewith is a conduit 26 for communicating the filtered gases from channel 28 to gas sensing mechanism 3 (see FIG. 1). It is to be understood that conduit 26 need not be in direct contact with hydrophobic member 22 so long as it is operatively coupled to housing 12 for communicating the flow of gas from channel 28 to the sensing mechanism. Conduit 26 has an outer surface 30 thereof, the diameter of which substantially approximates the inner diameter defined by inner wall 18 of housing 12. In this manner, outer surface 30 of conduit 26 may be coupled with the inner wall of housing 12 in a gas-tight and fluid-tight manner, as known to those of ordinary skill in the art.

Coupled with first end 14 of housing 12 is gas sampling line 32 having an outer diameter, defined by an outer surface 34, which substantially approximates the inner diameter of hydrophilic liner 20. The inner diameter of hydrophilic liner 20 is defined by an inner surface 36 thereof. Accordingly, outer surface 34 of the gas sampling line 32 may be coupled in a gas-tight and fluid-tight manner with inner surface 36 of the hydrophilic liner in a gas-tight and fluid-tight arrangement, as known to those of ordinary skill in the art.

The present invention completes that the internal volume of the cylindrical housing 12, which is defined by the inner surface 36 of the hydrophilic liner 20, the upstream surface 25 of the hydrophobic disk 22 and an outlet 37 of the gas sampling line 32 is 1.5 cc or less.

In operation, a patient expires gases containing liquids such as water, blood, mucus, medications and the like, into a nasal cannula (not shown), gas mask (not shown) or the like. Downstream of the nasal cannula, or other suitable respiratory collection mechanism, the expired gases leaves a mainstream conduit 2 (see FIG. 1) and enters gas sampling line 32 such that at least a portion of the gases are directed toward filter assembly 10. Gas sampling line 32 forms a conduit through which the expired gases enter filter assembly 10 through outlet 37 thereof. Upon entering the filter assembly, the gases still contain liquids such as water, blood, mucus, medications and the like and/or particulates, which are desirably substantially filtered from the gases prior to the gases being directed toward gas monitoring system 3.

As the expired gases proceed through channel 28 of housing 12, moisture is wicked out of the gas stream by hydrophilic liner 20 lining inner wall 18 and is locked away from the gas stream. While hydrophilic liner 20 is capable of absorbing a substantial portion of the moisture from the gas stream, some moisture will remain in the stream. Thus, hydrophobic member 22 is provided as a second line of defense against moisture reaching the gas monitoring system. As the gas stream reaches the area proximate second end 16 of housing 12, the stream encounters hydrophobic member 22. Because member 22 is formed of a hydrophobic material, gases will be permitted to pass therethrough but liquids will be substantially prevented from passing through the hydrophobic member. Instead, any liquid remaining in the gas stream will remain within channel 28 of cylindrical housing 12 and, preferably, will be absorbed by the downstream-most portion of hydrophilic liner 20.

As housing 12 is coupled in a gas-tight and fluid-tight arrangement with the outer surface of conduit 26, the only way that gases may exit channel 28 is through hydrophobic member 22. Thus, gases substantially free of liquids pass through the hydrophobic member 22, enter conduit 26 and proceed to the gas monitoring system to be monitored. In this manner, only gases substantially free of liquid condensate are permitted to reach the gas monitoring system. Further, because only inner wall 18 of housing 12 is lined with hydrophilic liner 20, the waveform of the exhaled gas sample is permitted to proceed substantially undisturbed from the point at which the sample is collected to the point at which the sensing mechanism readings are taken. Disturbance to the waveform which may be affected due to hydrophobic member 22 is of minimal consequence.

Figure 3:
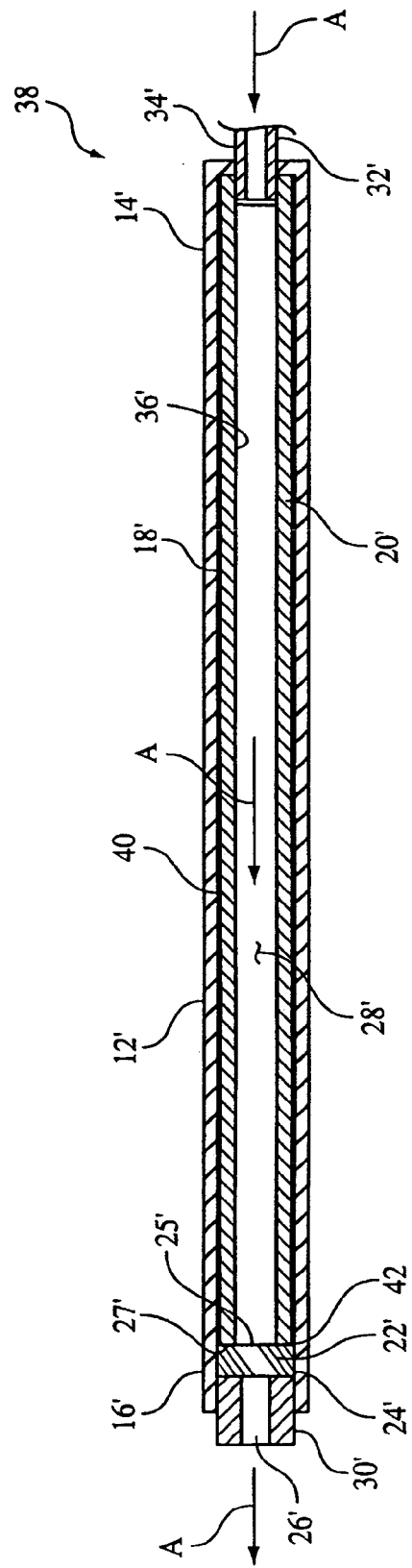
FIG. 3 is a cross-sectional view of a second embodiment of the filter assembly.

Referring now to FIG. 3, a second embodiment of a filter assembly according to the principles of the present invention is illustrated and denoted generally by, reference numeral 38. Like filter assembly 10 of FIG. 2, filter assembly 38 includes a housing 12' typically formed of a suitable polymer and having a cylindrical shape. Housing 12' has axially opposed first and second ends 14', 16' and an inner diameter defined by an inner wall 18' thereof. Lining inner wall 18' is a hydrophilic liner 20' for wicking moisture from expired gases and locking it away from the gas stream. The present invention contemplates that hydrophilic liner 20' be formed of a material suitable for accomplishing the wicking function, such as a porous plastic, having a pore size ranging from approximately 5 microns to approximately 50 microns. As discussed above, hydrophilic liner 20' not only absorbs moisture but also acts as a smooth lining for housing 12', and thereby minimizes the turbulence effects on the gas stream caused by rough walls.

Disposed between inner wall 18' of housing 12' and hydrophilic liner 20' is an absorbent layer 40. In an exemplary embodiment of the present invention, absorbent layer 40 has a thickness that is less than the thickness of hydrophilic liner 20' and is formed of an absorbent material having a greater absorbance than hydrophilic liner 20'. The present invention also contemplates that the absorbent layer can be as thick or thicker than the hydrophilic layer. Also, the absorbency of the absorbent layer need not be greater than that of the hydrophilic layer.

Absorbent layer 40 is coupled with inner wall 18' of housing 12' by any technique known to those of ordinary skill in the art including, but not limited to, adhesives. Similarly, hydrophilic liner 20' is coupled with the absorbent layer 40 by any known technique, e.g., hydrophilic adhesives.

In the illustrated exemplary embodiment, absorbent layer 40 lines inner wall 18' of housing 12' from first end 14' to a point where hydrophobic disk 22' is located, which is proximate second end 16'. In addition, hydrophilic liner 20' lines the absorbent layer 40' along substantially the entire length of the absorbent layer. It is to be understood, however, that absorbent layer 40 need not extend along the entire length of the housing, need not cover the entire surface of inner wall 18, and need not be formed from a single, unitary material. Rather, absorbent layer 40 can be formed from multiple pieces of material, and each portion or piece of the absorbent layer need not be formed from the same material. For example, the absorbent layer can be formed such that the absorbency of the material changes along the length of the housing or is maximized where it is more likely that condensation will gather.

As in the previous embodiment, a hydrophobic member 22' is positioned proximate second end 16' of housing 12'. Hydrophobic member 22' has an outer diameter, defined by an outer surface 24' thereof that approximates the inner diameter of the cylindrical housing 12' such that outer surface 24' is coupled with inner wall 18' of the cylindrical housing 12' in a gas-tight and fluid-tight arrangement, as known to those of ordinary skill in the art. In this manner, only gases passing through the hydrophobic member 22' are permitted to reach the sensing mechanism. In the illustrated embodiment, an upstream surface 25' of the hydrophobic member is in contact with a downstream edge 27' of hydrophilic liner 20' and a downstream edge 42 of absorbent layer 40'. However, the present invention also contemplates that there need not be direct contact between these members.

Positioned downstream of the hydrophobic member 22' and in contact therewith is a conduit 26' for communicating the filtered gases from housing 12' to the sensing mechanism. It is to be understood that conduit 26' need not be in direct contact with hydrophobic member 22', so long as it is operatively coupled to housing 12' for communicating the flow of gas from channel 28' to the sensing mechanism. An outer surface 30' of conduit 26' is coupled in a gas-tight and fluid-tight manner to the inner wall of housing 12' as described above in relation to FIG. 2.

Coupled with first end 14' of housing 12' is a gas sampling line 32'. An outer surface 34' of gas sampling line 32' is coupled in a gas-tight and fluid-tight manner to an inner surface 36' of hydrophilic liner 20' as described above in relation to FIG. 2.

In operation, a patient's expired gases enter gas sampling line 26' and filter assembly 38 as described above with reference to FIGS. 1 and 2. As the expired gases proceed through the internal volume of housing 12', moisture is wicked out of the gas stream by hydrophilic liner 20' and locked away from the gas stream. Further, liquids passing through hydrophilic liner 20' are further wicked therefrom and locked away from the gas stream by absorbent layer 40. In this manner, more liquid may be locked away from the gas stream than in the embodiment of FIG. 2. While hydrophilic liner 20' and absorbent layer 40 are capable of absorbing a substantial portion of the moisture from the gas stream, some moisture will remain in the stream. Thus, hydrophobic member 22' is provided as a second line of defense against moisture reaching the sensing mechanism. Because hydrophobic member 22' is formed of a hydrophobic material, gases will be permitted to pass therethrough but liquids will be substantially prevented from passing through the hydrophobic member 22'. Instead, any liquid remaining in the gas stream will remain within channel 28' and, preferably, will be absorbed by the downstream-most portions of hydrophilic liner 20' and absorbent layer 40.

As housing 12' is coupled in a gas-tight and fluid-tight arrangement with conduit 26', the only way that gases may exit housing 12 is through the hydrophobic member 22'. Thus, gases substantially free of liquids pass through the hydrophobic member 22', enter conduit 26' and proceed to the gas monitoring system to be monitored. In this manner, only gases substantially free of liquid condensate are permitted to reach the sensing mechanism. Further, because only inner wall 18' of housing 12' is lined with hydrophilic liner 20', the waveform of the exhaled gas sample is permitted to proceed substantially undisturbed from the point at which the sample is collected to the point at which the sensing mechanism readings are taken. Disturbance to the waveform which may be affected due to the hydrophobic member 22' is of minimal consequence.

Figure 4:
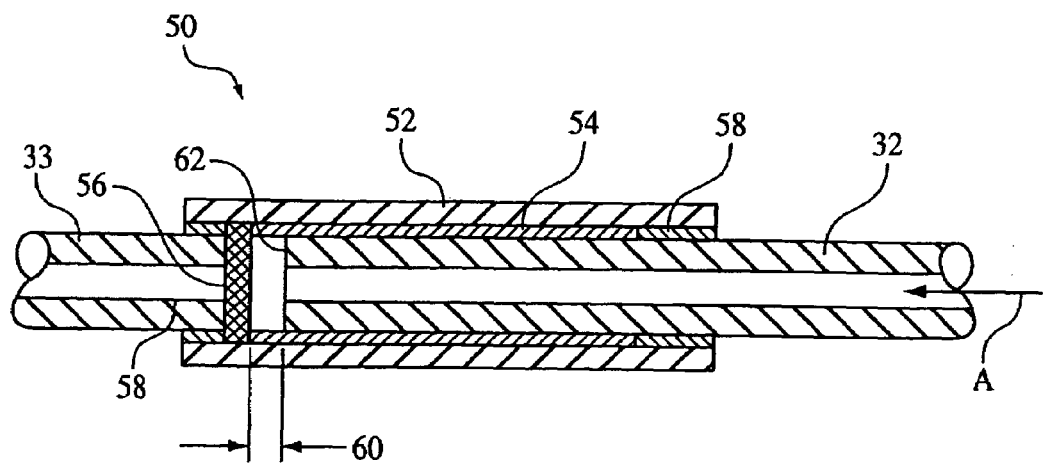
FIG. 4 is a cross-sectional view of a portion of a third embodiment of the filter assembly.

FIG. 4 is a cross-sectional view of a portion of a third embodiment of the filter assembly 50 according to the principles of the present invention. Filter assembly 50 includes a housing 52 connected to a sampling line 32 and to a exit sampling line 33. A hydrophilic member 54 is disposed in the housing between sampling line 32 and housing 52. A hydrophobic member 56 is provided across the diameter of the housing. Sealing elements 58 are provided at each end of the housing to connect the housing the inlet and outlet lines. Housing 52 can be made from any suitable material, such as plastic, rubber, or silicon. The present invention also contemplates that the housing can be formed, at least in part, from an absorbent material or a gas drying material that is able to remove water/fluid from the gas, such as NAFION® produced by DuPont.

The filter assembly of this embodiment is generally similar to that shown in FIG. 2, except that hydrophilic member 54 is disposed between sampling line 32 and the housing 52 so that only a fraction of the hydrophilic member is exposed to the gas stream, which is indicated by arrow A. Hydrophilic member 54 is positioned relative the flow of gas A such that the flow of gas impacts on the hydrophobic member. Gas passes through the hydrophobic member, but water and other liquid does not. Hydrophilic member 54 is positioned relative to hydrophobic member 56 such that any water or other liquid that accumulates on the surface to the hydrophilic member migrates to hydrophilic member 54.

To allow the water to migrate along the surface of hydrophobic member 56 to the hydrophilic member, a gap 60 is maintained between an end 62 of sampling line 32 and hydrophobic member 56. Gap 60 can be any size so long as water, or some other liquid depending on the liquid that is carried in gas stream A, is able to pass to hydrophilic member 54. This embodiment makes use of the wicking property of the hydrophilic member in that liquid that reaches the hydrophilic member is absorbed into the hydrophilic member and wicked away from hydrophobic member 56. The volume of hydrophilic member 54 is selected such that it is large enough to hold the quantity of water that may accumulate over its operating life.

To minimize resistance and its resulting effect on signal fidelity and rise time, hydrophobic member 56 has a width between 10 to 60 thousandths of an inch. The inside diameter of the sampling line an housing 52 should be sufficiently small to minimize mixing of the flowing gases as they travel through the filter assembly so that the signal fidelity/rise time is maintained.

Figure 5:
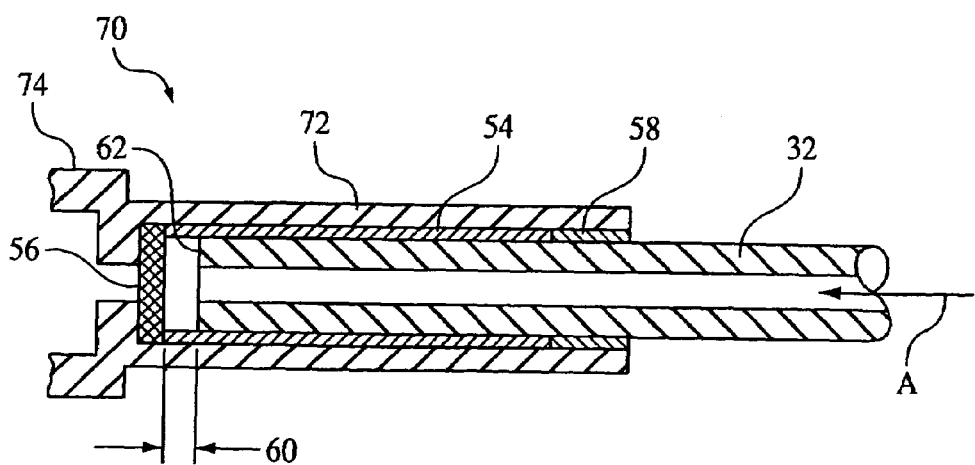
FIG. 5 is a cross-sectional view of a portion of a fourth embodiment of the filter assembly.

FIG. 5 is a cross-sectional view of a portion of a fourth embodiment of the filter assembly 70 that is similar in many respects to the filter assembly of FIG. 4. The primary difference between these two embodiment resides in the structure for housing 72. In the embodiment of FIG. 5, housing 72 includes a sample cell portion 74, such that the filter assembly is integral will the sample cell housing. That is, sample cell portion 74 houses the structures of the sample cell, which is the portion of the sampling system where the constituents of the gas are measured using irradiated energy or any conventional gas measurement technique. An example of an integrated filter and sample cell is taught in published PCT Appln. No PCT/US03/31916 (Publication No. WO 2004/033062), the contents of which are incorporated herein by reference.

Figure 6:
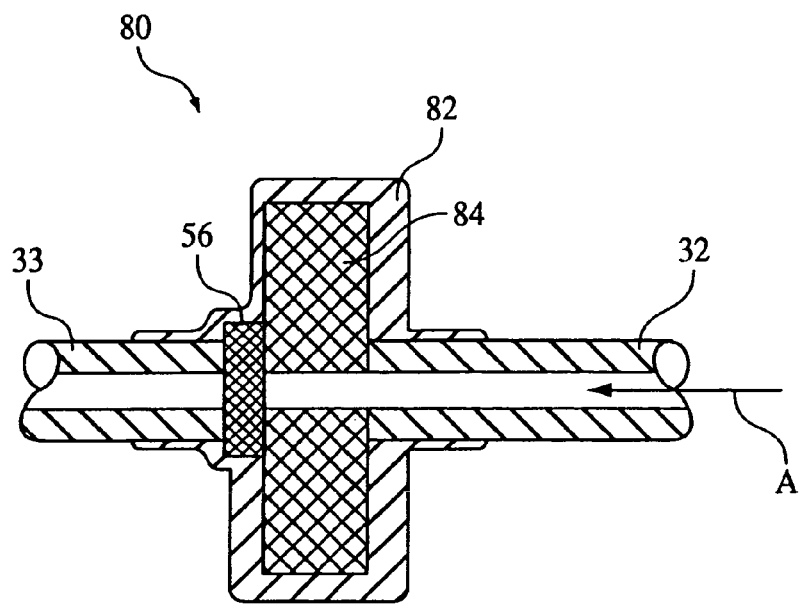
FIG. 6 is a cross-sectional view of a portion of a fifth embodiment of the filter assembly.

FIG. 6 is a cross-sectional view of a portion of a fifth embodiment of a filter assembly 80 according to the principles of the present invention. In this embodiment, a housing 82 contains a mass of hydrophilic material 84 as the hydrophilic member. The large mass of hydrophilic material 84 disposed proximate to hydrophobic member 56 facilitates wicking of liquids from the hydrophobic member. In the embodiments shown in FIGS. 4–6, hydrophobic member 56 and hydrophilic member 54 and 84 are circular or cylindrical-shaped. It is to be understood that other shapes for these components are contemplated by the present invention.

Figure 7:
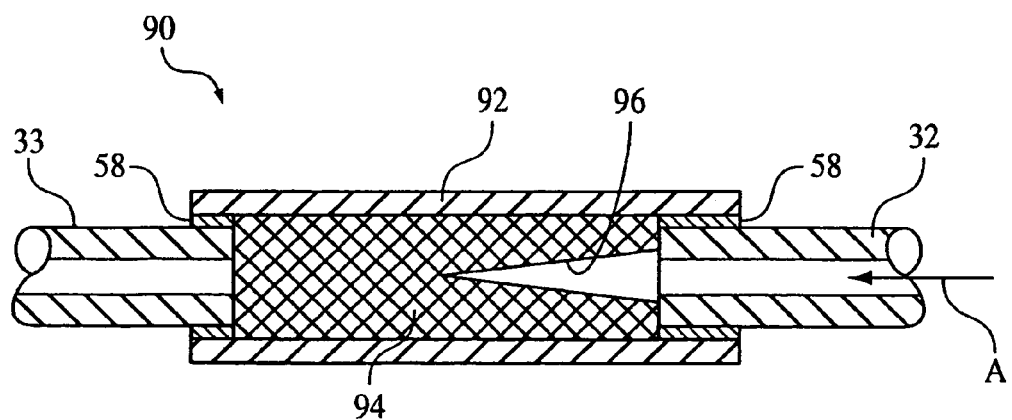
FIG. 7 is a cross-sectional view of a portion of a sixth embodiment of the filter assembly.

FIG. 7 is a cross-sectional view of a portion of a sixth embodiment of a filter assembly 90 according to the principles of the present invention. In the embodiment, the filter assembly includes a housing 92 that contains only a hydrophilic member 94. There is no hydrophobic member in this embodiment. Hydrophilic member 94 is relatively porous to allow gas to pass through it while also being sufficiently absorbent to remove any moisture in the gas as it passes through the hydrophilic member.

In the illustrated embodiment, a recess 96 is provided in the end of hydrophilic member 94 so that a relatively large surface area of the hydrophilic member is exposed to the incoming gas stream A. Providing a recess to increase the surface area of the hydrophilic member exposed to the incoming gas stream maximizes the ability of the hydrophilic member to capture contaminants/particulates while minimizing the pressure drop in the gas stream caused by the presence of the hydrophilic member. In the illustrated embodiment, recess 96 has a cone-shaped. It is to be understood, however, that the present invention contemplates other configurations for the recess, such as triangular or star-shaped. In addition, the hydrophilic member and housing can also have configurations other than the cylindrical shape shown in FIG. 7.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A filter assembly for use in a sidestream gas sampling assembly comprising:
   a housing having an inlet, an outlet, and an inner wall defining a channel through the housing from the inlet to the outlet;
   a hydrophobic member disposed across the channel at a location proximate to the outlet;
   a hydrophilic liner disposed on the inner wall; and
   an absorbent layer positioned between the inner wall and the hydrophilic liner.

2. The filter assembly of claim 1, wherein the absorbent layer has a first edge that contacts a surface of the hydrophobic member.

3. The filter assembly of claim 1, wherein the absorbent layer covers a majority of the inner wall extending between the inlet and the hydrophobic member.

4. The filter assembly of claim 1, wherein the absorbent layer has a substantially smoother inner surface.

5. The filter assembly of claim 1, wherein the hydrophilic liner covers a majority of an absorbent layer extending between the inlet and the hydrophobic member.

6. The filter assembly of claim 1, wherein the hydrophilic liner has a first edge that contacts a surface of the hydrophobic member.

7. The filter assembly of claim 1, wherein the hydrophilic liner covers a majority of the inner wall extending between the inlet and the hydrophobic member.

8. The filter assembly of claim 1, further comprising a gas sampling line coupled to the inlet.

9. The filter assembly of claim 8, further comprising an exit conduit coupled to the outlet.

10. The filter assembly of claim 1, wherein the housing is cylindrical and wherein the hydrophobic member is disc-shaped.

11. A sidestream gas monitoring system comprising:
   (a) a sampling line having a first end and a second end, wherein the sampling line is adapted to carry a flow of gas from a patient circuit;
   (b) a filter assembly comprising:
      (1) a housing having an inlet adapted to be coupled to the second end of the sampling line, an outlet, and an inner wall defining a channel through the housing from the inlet to the outlet,
      (2) a hydrophobic member disposed across the channel at a location proximate to the outlet,
      (3) a hydrophilic liner disposed on the inner wall, and
      (4) an absorbent layer positioned between the inner wall and the hydrophilic liner;
   (c) a sample cell operatively coupled to an outlet of the housing; and
   (d) a detecting system adapted to measure a constituent of gas contained within the sample cell.

12. The system of claim 11, wherein the absorbent layer has a first edge that contacts a surface of the hydrophobic member.

13. The system of claim 11, wherein the absorbent layer covers a majority of the inner wall extending between the inlet and the hydrophobic member.

14. The system of claim 13, wherein the hydrophilic liner covers a majority of the absorbent layer extending between the inlet and the hydrophobic member.

15. The system of claim 11, wherein the hydrophilic liner has a first edge that contacts a surface of the hydrophobic member.

16. The system of claim 1, wherein the hydrophilic liner covers a majority of the inner wall extending between the inlet and the hydrophobic member.

17. The system of claim 1, wherein the housing is cylindrical and wherein the hydrophobic member is disc-shaped.

18. A filter assembly for use in a sidestream gas sampling assembly comprising:
   a housing having an inlet, an outlet, and an inner wall defining a channel through the housing from the inlet to the outlet;
   hydrophilic member having a first end portion and a second end portion, wherein the hydrophilic member is disposed in the housing such that gas entering the housing impacts the first end portion and such that gas passing through the channel must pass through at least a portion of the hydrophilic member, and wherein the first end portion includes a recess defined therein.

19. The filter assembly of claim 18, wherein the recess is coaxially aligned with a longitudinal axis of the inlet of the housing.

20. The filter assembly of claim 18, wherein the recess is generally cone-shaped.

* * * * *